United States Patent [19]

Sztejnberg

[11] Patent Number: 5,190,754
[45] Date of Patent: Mar. 2, 1993

[54] *AMPELOMYCES QUISQUALIS* AQ10, CNCM I-807, FOR BIOLOGICAL CONTROL OF POWDERY MILDEW

[75] Inventor: Abraham Sztejnberg, Rehovot, Israel

[73] Assignee: Yissum Research Development Company of the Hebrew University of Jerusalem, Jerusalem, Israel

[21] Appl. No.: 785,157

[22] Filed: Oct. 31, 1991

Related U.S. Application Data

[63] Continuation of Ser. No. 385,470, Jul. 27, 1989, abandoned.

[30] Foreign Application Priority Data

Aug. 2, 1988 [IL] Israel .......................................... 87323

[51] Int. Cl.$^5$ .......................... A61K 37/00; C12N 1/12; C12N 1/06; C12N 1/14
[52] U.S. Cl. ................................ 424/93 Q; 435/254; 435/259; 435/800; 435/911
[58] Field of Search ............... 435/254, 259, 800, 911; 424/93

[56] References Cited

PUBLICATIONS

Beuther et al. (1983), Demonstration of Polysaccharid-Degrading Enzymes in Culture Filtrates of the Powdery Hyperparasite, *Ampelomyces quisqualis*, *Phytopath. Z.*, 106 365-368.

Philipp, W. D. (1985), Extracellular Enzymes and Nutritional Physiology of *Ampelomyces quisqualis* Ces., of Powdery Mildew, in vitro, *Phytopath. Z.* 114 274-283.

Philipp, et al.; Mycoparasitism of *Ampelomyces quisqualis* on Powdery Mildew of Cucumber and Other Vegetable Species; *Journal of Plant Diseases and Protection* (1979); pp. 129-142.

Steinberg, et al.; *Ampelomyces quisqualis* for Biological and Integrated Control of Powdery Mildew; *Phytoparasitica* (1988); 16:1, p. 69.

Galper, et al.; Scanning Electron Microscopy of the Ontogeny of *Ampelomyees quisqualis* Pycnidia; *Can. J. Microbiol* (1985); 31: 961-964.

Steinberg, et al.; *Ampelomyces quisqualis* for Biological and Integrated Control of Powdery Mildews in Israel; *J. Phytopathology* (1989); 4: 285-295.

Sztejnberg "Field Biocontrol of Mango Powdery Mildew by *Ampelomyces quisqualis*", 5th International Congress of Plant Pathology, Aug. 20-27, 1988.

Sundheim et al. (1982) *Plant Pathology* 31: 209-214 "Control of Cucumber Powdery Mildew by the Hyperparasite *Ampelomyces quisqualis* and Fungicides".

Phillip et al. (1982) *Journal of Plant Diseases and Protection* 89: 375-381 "Investigations on the Effect of Fungicides on *Ampelomyces quisqualis* with Regard to Integrated Control . . . ".

*Primary Examiner*—David M. Naff
*Attorney, Agent, or Firm*—Foley & Lardner

[57] ABSTRACT

A novel fungal strain of the species *Ampelomyces quisqualis* has been isolated and pure cultures thereof prepared. This novel strain is termed AQ10 and has CNCM Accession Number I-807, and was found to be a hyperparasite of the causative fungi of powdery mildew. Conidia obtained from this novel strain or mutants thereof may be formulated into phytological compositions and used effectively as a biocide for controlling powdery mildew infestations.

7 Claims, No Drawings

AMPELOMYCES QUISQUALIS AQ10, CNCM I-807, FOR BIOLOGICAL CONTROL OF POWDERY MILDEW

This application is a continuation of application Ser. No. 07/385,470, filed Jul. 27, 1989, now abandoned.

FIELD OF INVENTION

The present invention is in the field of biological control of pests and more specifically concerns the biological control of powdery mildew (PMD), by a hyperparasite of the causative microorganism of PMD.

BACKGROUND OF THE INVENTION AND PRIOR ART

In recent years there has been a growing interest in biological control of agricultural pests, i.e. by the use of microorganisms antagonistic to the pest, in view of the hazardous environmental effects of conventional chemical pesticides. Such a control has the advantage of being target specific and not polluting the environment.

PMD is a plant disease of world wide occurrence caused by various types of fungi which can infect many types of trees, flower plants, vegetables, fruit plants and various field crops, all of which will be referred to hereinafter collectively as "agricultural plants". A PMD infection is evidenced by a superficial, white or light grey powdery or felty growth on the surface of leaves, buds, young shoots, inflorescences, fruits and even flowers. In many cases the result of a PMD infection in agricultural plants is the reduction of the yields and quality of crop.

Up to date, no microorganisms which have the capability to combat PMD have been found. There has been a suggestion in the art (Wolf-Dieter Philipp and Gerd Cruger, Journal of Plant Diseases and Protection 86 (3), 129-142 (1979), to utilize a hyperparasite to the causative microorganisms of PMD, but all hyperparasites that have been isolated prior to the present invention, were found to have insufficient effectivity for the control of PMD in agricultural plants in the field in or in a greenhouse.

It is the object of the present invention to provide a pure culture of a hyperparasite of the causative microorganism of PMD, which may be utilised for controlling PMD.

SUMMARY OF THE INVENTION

In accordance with the present invention, a novel fungal strain belonging to the fungal species *Ampelomyces quisqualis* has been isolated and termed AQ10. It was found that AQ10 is a hyperparasite of the causative fungi of PMD. It was further found in accordance with the invention that the conidia of AQ10 are potent anti-PMD agents that can be used effectively for combatting PMD in agricultural plants whereby a long felt want is satisfied for the first time.

Thus in accordance with the present invention, there is provided a pure culture of the strain AQ10 which was deposited in the culture collection of the Institut Pasteur (Collection Nationale de Cultures de Microorganismes-CNCM) on Oct. 10, 1988, and accorded the designation I-807.

A pure culture of AQ10 may be subjected to a controlled mutagenic treatment, such as by various radioactive substances, chemical mutagens or by irradiation with $\gamma$- or X-rays, in order to obtain a mutant of the AQ10 strain whose conidia is also an antagonist of causative fungi of PMD and which may have some improved properties such as a higher potency, improved reproduction rate, improved susceptibility to storage and the like.

Conidia are the asexual reproductive spores of fungal microorganisms. The conidia of AQ10 are easily obtained in a substantially pure form from the AQ10 pure culture.

Thus, the present invention also provides an essentially pure aqueous suspension of AQ10 conidia.

Furthermore, the present invention provides an aqueous anti-PMD composition comprising an effective amount of conidia of AQ10 or of a mutant thereof, and, if desired, with phytologically acceptable additives compatible with said conidia.

Still further, the invention provides a method of controlling PMD in agricultural plants, comprising applying onto the plants an effective amount of conidia of AQ10 or of a mutant thereof. Such a treatment, which may be periodically repeated, is effective for destroying the causative microorganism of PMD, for inhibiting its proliferation as well as for preventing future PMD infestation.

The control of PMD in accordance with the invention may be effected in an open field or in a greenhouse. For prophylatic application, the conidia should be so formulated as to ensure their viability until onset of a PMD infestation whereupon they start immediately to exert their hyper-parasitic activity.

A DETAILED DESCRIPTION OF THE INVENTION

Conservation and Storage of the Cultures

The pure cultures of AQ10 may be conserved for some time in media which are suitable for fungal growth and proliferation. An example of such a medium is an agar substrate, which comprises wheat-bran extracts.

Due to the consumption of nutrition by AQ10 and the secretion of waste products, a sample of the culture comprising cells of AQ10 or conidia produced thereby should be transferred regularly into a new, fresh medium, e.g. once every three to four weeks. If the culture is growing on an agar substrate, conidia which are produced by the micro-organism can be harvested and then seeded onto a new agar substrate. Harvesting of the conidia is suitably performed by the addition of distilled water onto the agar substrate, and due to hypertonic pressure the ripe conidia are excreted into the supernatant fluid where they can easily be collected.

However, periodical transfer of conidia into new media may give rise to a mutagenic stress and in consequence a genetic drift of the culture may occur. Thus, such conservation of the culture is suitable mainly for short periods of time.

For storage periods of up to about 6 months, a monolayer of the AQ10 cells on a solid matrix, such as BEA (bran extract agar), is kept at 4° C.

A suspension of AQ10 conidia in an aqueous solution comprising about $10^7$ conidia/ml, which is obtained by fermentation (see below), may be stored for longer periods, i.e. up to about 12 months. The conidia probably secrete antibiotic compounds which inhibit growth of other microorganisms, and in order for the inhibition to be effective a concentration of conidia of the order specified is required.

Long term storage may also be achieved by freeze drying the conidia. Such freeze dried conidia preserve their viability over prolonged storage periods.

II Fermentation

Fermentation is required in order to obtain large quantities of AQ10, for the preparation of anti-PMD compositions. Fermentation may either be in liquid media such as potato broth (which is the soluble extract of boiled potatoes), corn-steep liquor (which is a syrup remaining after boiling of corn seeds in the starch industry), cotton meal extract (the extracted composities of cotton seed meal following boiling), whey, wheat-bran or a combination thereof, or may be carried out in a semi-solid medium, i.e. a wet particulate solid substrate, e.g. powdered carriers such as vermiculite and peat-moss or within wet granulated matrices such as of sorghum, wheat or barley grains.

Liquid fermentation is performed by inoculating a sample of AQ10 into a growth medium and aerobically incubating the medium for a sufficient amount of time. The optimal temperature for fermentation was found to be about 25° C. and the optimal pH about 6.5 to about 8.0. Fermentation is preferably carried out under agitation e.g. in shaking flasks. Under such optimal conditions it is possible to obtain within seven to nine days a yield of about $1.5-2.0 \times 10^7$ conidia/ml.

A suitable medium for performing the fermentation is potato broth. In this medium the yield of conidia after seven to nine days incubation is about 10 fold that of the other media listed above. However, it was found that a similar yield of conidia is achieved when utilising a whey medium supplemented with corn steep liquor with the relative volume of whey to corn steep liquor being about 2:1. Against this it was found in accordance with the invention that under certain conditions AQ10 grows and proliferates better in the dark. Therefore, in accordance with the invention fermentation of AQ10 is sometimes preferably carried out in the dark.

Semi-solid fermentations may be carried out on a number of carriers as specified above. The final number of conidia which can be harvested after such fermentation is higher than that achieved with liquid fermentation, although the fermentation time, which depends on the carrier type, is usually longer.

III Formulation of Anti-PMD Compositions

AQ10 conidia are generally applied onto the agricultural plants by spraying an aqueous composition containing about $10^6$ conidia/ml.

For effective treatment an aqueous composition of AQ10 conidia should be spread so as to cover the whole surface of the leaves and the other plant organs such as inflorescences, fruits or flowers, which are infected with PMD. When water is sprayed onto a waxy surface such as leaves, wetting is incomplete as drops tend to form. Consequently the aqueous anti-PMD compositions according to the invention preferably contain additives such as surfactants or wetting agents, e.g., so-called thinners, which are typically added in an amount of 0.2% w/w.

Since the anti-PMD AQ10 microorganism according to the invention is a hyperparasite of the causative microorganisms of PMD, no nutrients have to be incorporated in the compositions. However, at times it may be desirable to add such nutrients and also protectants to help keep the conidia viable, such as for example when the compositions are to be used for prophylactic treatment for which it is necessary that the micro-organisms will be viable for long periods of time.

DESCRIPTION OF SOME SPECIFIC EMBODIMENTS

In the following description some specific embodiments will be described, it being understood that the invention is not limited thereto and that various modifications within the scope of the claims are possible.

EXAMPLE 1

Culture of AQ10

AQ10 was incubated on plates which contained BEA substrate.

For the preparation of BEA, 100 g of wheat-bran were dissolved in 1 liter of distilled water, and the solution was then sterilised in an autoclave for twenty minutes in order to extract the wheat bran and thereafter filtered through gauze filters, (20 $\mu$m pores). Following autoclaving and subsequent filtration, water was supplemented to 1 liter, and 20 g of malt extract, 2 g of DL-asparagine and 20 g of agar were admixed into the solution, which was then autoclaved and poured into agar plates and cooled.

After three weeks of incubation, 10 ml distilled water was added to each plate and due to the hypertonic pressure, the ripe conidia were excreted into the supernatant where they were collected, the yield being about $10^7$ to $10^8$ conidia/ml.

The harvested conidia were then either replated on fresh BEA plates, freeze dried and stored at 4° C. or used for fermentation.

EXAMPLE 2

Storage of AQ10

(a) Storage of Monolayers of AQ10

AQ10 conidia were seeded onto a BEA plate, prepared as in Example 1, and incubated for 14 days until a monolayer of AQ10 was obtained. The agar plate was then stored at 4° C., with no loss of cell viability for at least six months.

(b) Storage of Conidial Suspensions

Seeding of AQ10 on BEA plates and harvesting of conidia were performed in accordance with Example 1. The conidial suspension containing about $10^7$ to $10^8$ conidia/ml was then stored at 4° C. for up to 12 months, with no apparent loss in their viability.

During this term no contamination by other fungi or by bacteria was observed, probably due to a secretion of antibiotic substances present in the conidia preparation.

(c) Freeze Drying of Conidia

A suspension of $10^6$ conidia/ml, was centrifuged at 12000 g for 10 min. after which the resulting pellet was resuspended with 10% skimmed milk. Thereafter, the suspension was frozen in dry ice-acetone, lyophilized, and thereafter stored at −4° C. Rehydration was achieved by adding sterile water to the lyophilized conidia.

After three months there were essentially no signs of loss in viability when replated onto BEA plates.

EXAMPLE 3

Fermentation (a) Liquid Fermentation in Various Growth Media

A sample of 100 ml of conidia, containing about $10^6$ conidia/ml, was inoculated into flasks containing each 1 liter of a fermentation medium having a pH between 6.5–8.0. Each of the flasks contained a different medium. The incubation temperature was about 25° C. During incubation the flasks were shaken, and after nine days, the yield of conidia was determined. The results are in the following Table 1:

TABLE 1

| | AQ10 | |
|---|---|---|
| | Yield of conidia ($\times 10^6$/ml) | |
| Growth medium | Average* | Maximal |
| a) 10% Wheat-bran | 9.2 | 10.0 |
| b) 20% Potato Extract | 12.9 | 17.0 |
| c) 20% Whey | 2.1 | 3.9 |
| d) 20% Whey + 7.5 g Cotton Meal Extract | 4.6 | 5.5 |
| e) 10% Whey + 6 ml Corn Steep Liquor (CSL) | 10.6 | 13.0 |
| f) 20% Whey + 14 ml CSL | 12.3 | 17.0 |
| g) 20% Whey + 12 ml CSL | 16.0 | 19.0 |

*Four replicates

It may be seen from the above results, that the highest yield with a medium of a single source is obtained in 20% potato extract. However a combination of 20% whey with CSL, gave an even higher yield.

(b) The Effect of Light on AQ10 Growth

A sample of a suspension of AQ10 conidia containing $10^6$ conidia/ml, was in one experiment seeded on a BEA substrate, contained in petri dishes or inoculated into a potato/dextrose (PD) liquid media and in another experiment inoculated into a liquid sucrose media. Some of the AQ10 cultures were either exposed to sunlight during daytime throughout the incubation, while others were darkened by covering them with aluminium foil. The temperature and pH were as above. After 10–14 days of incubation, the yield of conidia was determined, and the results are represented in the following Table 2:

TABLE 2

| | Total No. of Conidia | |
|---|---|---|
| Growth Medium | LIGHT | DARK |
| Liquid sucrose | $1.6 \times 10^8$ | $1.9 \times 10^9$ |
| PDB | $3.0 \times 10^7$ | $9.0 \times 10^8$ |
| BEA/agar | $6.0 \times 10^5$ | $3.0 \times 10^7$ |

It is clear from the above results, that under the conditions described far better yields are achieved when AQ10 is grown in the dark.

(c) Semi-solid Fermentation

Sorghum grains were mixed with an AQ10 conidia suspension containing about $10^6$ conidia/ml. The mixture was then incubated in a dark container.

After 20 days of incubation $6 \times 10^7$ conidia/ml were obtained.

EXAMPLE 4

Formulation of AQ10 Conidia (a) Field Tests

Marrow squash plants in the open field were infected with PMD. Plants in a 0.25 acre plot were divided into groups of about 40 plants each, each group receiving one of the following treatments:

1. Spraying of an AQ10 conidia aqueous suspension such as obtained by fermentation in accordance with Example 3(a) using Growth Medium b) of Table 1. Altogether four separate sprays were made, each carried out within five days from the previous one.

2. Spraying of each of the following conventional chemical fungicides: Afugan (Hoechst, FRG), Magen (Nippon Soda Company Ltd. Japan), San619 (Sandoz, Switzerland), Ofir (Ciba Geigy, Switzerland). In each case three separate sprays were carried out as in (1) above.

3. Spraying of Tilt (Ciba Geigy, Switzerland), which is a systemic fungicide. Altogether three sprays were carried out as in (1) above.

4. Untreated control

The squash was handpicked every two days and crops of the four groups were kept separately and was divided into first and second rate quality, and weighed. The results are summarized in the following Table 3:

TABLE 3

| | Crop in Kg | | | | | |
|---|---|---|---|---|---|---|
| Quality rating | Untreated control | $AQ_{10}$ | Ophir | Afugan | Magen | San619 | Tilt |
| 1st quality | 90.3 | 113.7 | 119.6 | 134.5 | 125.3 | 128.7 | 151.5 |
| 2nd quality | 30.2 | 53.4 | 38.4 | 49.3 | 59.3 | 61.0 | 71.0 |
| Total: | 120.5[c] | 167.1[b] | 158.0[b] | 183.0[b] | 184.6[b] | 189.7[b] | 222.5[a] |

The letters against the Totals indicate statistic significance: All Totals marked with a "b" are not significantly different from one another. The Total marked with "a" is significantly different from the one marked with "c", and both are significantly different from the Totals marked with "b".

Despite the dry and hot weather, good hyperparasitism of AQ10 on PMD was observed throughout the season, as evidenced by microscopic observation of leaf samples.

Highest crop yield was obtained with tilt, which is a new chemical fungicide to which no resistance has as yet developed. AQ10 gave a crop yield similar to those obtained with the other fungicides, and significantly better than in the untreated control.

(b) Control of PMD in Mango Trees

Thirty six mango trees, in an organic farm in the Golan Heights, Northern Israel were divided into four groups each consisting of nine trees. Two groups of trees were treated with an AQ10 composition of according to the invention, which was applied to each group with a different repetition rate. A third group served as an untreated control and the fourth was treated with sulphur, which is the conventional treatment against PMD in organic agriculture. The extent of PMD control was evaluated by counting the number of fruits as well as determining the average weight of total fruit per tree. The results are shown in the following Table 4:

TABLE 4

| Treatment | Average number of fruit/tree: | Average weight of fruit/tree (kg) |
|---|---|---|
| non-treated control | 26 ± 12$^a$ | 12.50 ± 5.8$^a$ |
| AQ10 every 5 days (6 wks) | 48 ± 12$^b$ | 20.9 ± 4.9$^b$ |
| AQ10 every 7 days (6 wks) | 45 ± 15$^b$ | 19.32 ± 7.6$^b$ |
| Sulphur treatment (as commonly used in organic plots) | 35 ± 15$^{ab}$ | 15.72 ± 6.6$^{ab}$ |

The letters against the average numbers and average weight of fruits per tree indicate statistic significance: The numbers marked with "a" are significantly different from the numbers in the same column marked with "b"; the numbers marked with "ab" are not significantly different from the rest in the same column.

The fruit yield from the AQ10 treatment is significantly higher than the non-treated control and is also superior to the conventional sulphur treatment.

I claim:

1. A biologically pure culture of *Ampelomyces quisqualis* AQ10, Accession Number I-807.

2. An aqueous suspension of conidia of a biologically pure culture of *Ampelomyces quisqualis* AQ10, Accession Number I-807.

3. A biologically pure culture of a mutant of *Ampelomyces quisqualis* AQ10, CNCM Accession Number I-807, capable of providing the powdery mildew disease preventing activity of said *Ampelomyces quisqualis* AQ10.

4. An aqueous suspension of conidia of a biologically pure culture of a mutant of *Ampelomyces quisqualis* AQ10, CNCM Accession Number I-807, according to claim 3.

5. A composition for biological control of powdery mildew disease which contains conidia of a biologically pure culture of *Ampelomyces quisqualis* AQ10, CNCM Accession Number I-807, or of a mutant thereof capable of providing the powdery mildew disease preventing activity of said *Ampelomyces quisqualis* AQ10, and at least one phytologically acceptable additive compatible with said conidia.

6. A composition according to claim 5, wherein said additive is a surfactant.

7. A method of controlling powdery mildew infestation and infection in agricultural plants in the open field and greenhouse, comprising applying to plants conidia of a biologically pure culture of *Ampelomyces quisqualis* AQ10, CNCM Accession Number I-807, or a mutant thereof capable of providing the powdery mildew disease preventing activity of said *Ampelomyces quisqualis* AQ10, in an amount effective to prevent said infestation or infection.

* * * * *